(12) United States Patent
Pazenok et al.

(10) Patent No.: US 11,180,441 B2
(45) Date of Patent: Nov. 23, 2021

(54) METHOD FOR PREPARING SUBSTITUTED 4-AMINOINDANE DERIVATIVES

(71) Applicant: Bayer Aktiengesellschaft, Leverkusen (DE)

(72) Inventors: Sergii Pazenok, Solingen (DE); Christoph Saemann, Duesseldorf (DE); Yuriy Shermolovich, Kyiv (UA)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 16/624,183

(22) PCT Filed: Jun. 20, 2018

(86) PCT No.: PCT/EP2018/066396
§ 371 (c)(1),
(2) Date: Dec. 18, 2019

(87) PCT Pub. No.: WO2019/002042
PCT Pub. Date: Jan. 3, 2019

(65) Prior Publication Data
US 2020/0172468 A1 Jun. 4, 2020

(30) Foreign Application Priority Data
Jun. 27, 2017 (EP) .................... 17178090

(51) Int. Cl.
*C07C 209/54* (2006.01)
*C07C 211/60* (2006.01)

(52) U.S. Cl.
CPC .......... *C07C 209/54* (2013.01); *C07C 211/60* (2013.01)

(58) Field of Classification Search
CPC ... C07C 209/54; C07C 209/62; C07C 211/60; C07C 231/12
USPC ....................................... 564/308
See application file for complete search history.

(56) References Cited

U.S. PATENT DOCUMENTS

| 5,521,317 | A | 5/1996 | Briner |
| 9,199,941 | B2 | 12/2015 | Coqueron et al. |
| 9,249,104 | B2 | 2/2016 | Maechling et al. |
| 9,375,004 | B2 | 6/2016 | Benting et al. |
| 9,975,855 | B2 | 5/2018 | Coqueron et al. |

FOREIGN PATENT DOCUMENTS

| EP | 0256503 A2 | 2/1988 |
| EP | 0654464 A1 | 5/1995 |
| JP | 1117864 A | 5/1989 |
| WO | 9212970 A1 | 8/1992 |
| WO | 2010109301 A1 | 9/2010 |
| WO | 2012065947 A1 | 5/2012 |
| WO | 2012084812 A1 | 6/2012 |
| WO | 2013167545 A1 | 11/2013 |
| WO | 2013167549 A1 | 11/2013 |
| WO | 2014103811 A1 | 7/2014 |

OTHER PUBLICATIONS

Oda et al., "Structure-Activity Relationships of N-1,1,3-Trimethylindan-r-yl) carboxamide Fungicides" J. Pesticide Sci. 1993, vol. 18: 245-251.
Erickson and Mcloughlin., "Hydrogen Bond Donor Properties of Difluoromethyl Group" J. Org. Chem. 1995, vol. 60: 626-1631.
Oda et al., "Structure-Activity Relationships of 2-Chloropyridine-3-carboxamide Fungicides", Journal of Pesticide Science, 1992, vol. 17: pp. 91-98.
Cliffe et al., "The Acid-catalysed Rearrangement of Tetrahydroquinoline Derivatives" Journal of the Chemical Society C: Organic, 1966, 514-517.
International Search Report issued in counterpart application No. PCT/EP2018/066396, dated Aug. 9, 2018.
Oda, et al., "Quantitative Structure-Activity Relationships of 2-Chloropyridine-3-carboxamide Fungicides," J. Pesticide Sci., (1993), vol. 18: 49-57.

*Primary Examiner* — Ana Z Muresan
(74) *Attorney, Agent, or Firm* — McBee Moore & Vanik, IP, LLC

(57) ABSTRACT

The present invention relates to a method for preparing substituted 4-aminoindane derivatives of the general formula (I)

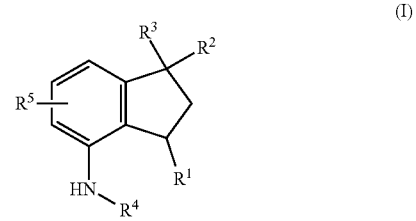

by rearrangement of compounds of the formula (II) in HF, wherein $R^1$, $R^2$, $R^3$, $R^4$, and $R^5$ have the definitions as specified in the description.

15 Claims, No Drawings

US 11,180,441 B2

METHOD FOR PREPARING SUBSTITUTED 4-AMINOINDANE DERIVATIVES

CROSS-REFERENCE TO RELATED APPLICATIONS

This application is the National Stage entry of International Application No. PCT/EP2018/066396, filed 20 Jun. 2018, which claims priority to European Patent Application No. 17178090.1, filed 27 Jun. 2017.

BACKGROUND

Field

The present invention relates to a process for preparing substituted aminoindane derivatives by rearrangement of a compound of the formula (II) in anhydrous HF.

Description of Related Art

4-Aminoindanes and derivatives are important intermediates for the preparation of bioactive compounds which can be used specifically for controlling harmful microorganisms in crop protection.

For instance, it is known that various pyrazole indanyl carboxamides have fungicidal activity (e.g. WO 1992/12970, WO 2012/065947, *J. Org. Chem.* 1995, 60, 1626 and WO 2012/084812).

It is also known that various pyridine indanyl carboxamides have fungicidal activity (e.g. EP-A 0256503, JP-A 1117864, *J. Pesticide Sci.* 1993, 18, 245).

In addition, it is known that some benzoyl indanyl amides have fungicidal activity (WO 2010/109301).

Chemical syntheses of 4-aminoindane derivatives have been described in the literature, but only allow the preparation of 4-aminoindanes with very limited substitution patterns (WO 2010/109301, WO 2014/103811, EP 0654464, U.S. Pat. No. 5,521,317). For instance, the methods described in WO 2010/109301 and in WO 2014/103811 only allow the synthesis of the 1,1,3-trimethyl-4-aminoindane derivative starting from aniline by condensation with acetone and exploit the rearrangement reaction described in EP 0654464 and U.S. Pat. No. 5,521,317.

A further possibility to prepare 4-aminoindane derivatives is described in WO 2013/167545 and WO 2013/167549. The synthesis is based on a Buchwald-Hartwig amination and thus enables a general synthetic route to substituted 4-aminoindanes. Disadvantages of this method are firstly the cost-intensive use of transition metal catalysts and secondly the problematic synthesis of the corresponding halo-substituted indane precursors. Furthermore, the amino function cannot be introduced directly by free $NH_3$, but rather requires the use of cost-intensive, protected ammonia derivatives.

EP 0654464 discloses a process for the preparation of 4-amino-1,1,3-trimethylindane, wherein 1-(2-acetoxypropionyl)-1,2,3,4-tetrahydro-2,2,4-trimethylquinoline (i.e. 1-oxo-1-(2,2,4-trimethyl-3,4-dihydroquinolin-1(2H)-yl) propan-2-yl acetate) was added over 45 minutes to 98% $H_2SO_4$ at 25-60° C. (exotherm). After stirring for a further 30 minutes at 60° C., water containing acetic acid was cautiously added dropwise and the mixture was heated at 100° C. for 3 hours. Petrol (60/80 b.p.) was added and the mixture basified to pH 9 with 35% aqueous ammonia. Separation of the organic layer, drying ($MgSO_4$) and solvent flash gave the desired product 4-amino-1,1,3-trimethylindane in 69% yield (EP 0654464, Example 1.B (iii)). In view of the achieved yield, this prior art process for producing 4-amino-1,1,3-trimethylindane needs to be improved. Moreover, the process according to EP 0654464 produces high amounts of liquid waste, namely a water solution of ammonium sulfate: $H_2SO_4$ used during the process needs to be neutralized with ammonia (as outlined above: 35% aqueous ammonia) in order to isolate the desired aminoindane derivative, since the latter easily forms a water soluble salt with $H_2SO_4$. Such a waste production is disadvantageous since it is not environmentally friendly.

Cliffe et al. (*J. Chem. Soc.* (C), 1966, 514-517: "*The Acid-catalyzed Rearrangement of Tetrahydroquinoline Derivatives*") disclose a method for preparing substituted aminoindane derivatives by rearrangement of a quinoline compound or a related compound in $H_2SO_4$ or $HNO_3$—$H_2SO_4$ or polyphosphoric acid, wherein the reaction is performed at 100° C. over 1 hour. This process is not environmentally friendly since for the isolation of the product from $H_2SO_4$, the latter should presumably be completely neutralized, producing high amounts of liquid waste similar as outlined above.

WO 2014/103811 describes the preparation of 4-amino-1,1,3-trimethylindane via isomerization of N-acetyl-2,2,4-trimethyltetrahydroquinoline, "which was heated to 90°, added dropwise to 98 wt. % sulfuric acid ($H_2SO_4$) and kept at 60°, followed by adding the reaction mixture into hot water (98° C.), heating the resulting mixture at 105° for 4 hours, neutralization with 27 wt. % aqueous sodium hydroxide solution (NaOH solution), and extraction with toluene to give a solution. of 4-amino-1,1,3-trimethylindane in toluene (190.4 g of a toluene solution containing 39.1 wt. % 4-amino-1,1,3-trimethylindane with 92.6% purity and a yield of 76.4% "(WO 2014/103811, Reference Example 1-3). This process is not environmentally friendly since for the isolation of the product from $H_2SO_4$, the latter should be completely neutralized upon addition of NaOH, producing huge amounts of waste.

With regard to the disadvantages outlined above, there is a demand for a simplified method that can be carried out industrially and economically for the general preparation of substituted 4-aminoindane derivatives from an available compound of the formula (II). The substituted 4-aminoindane derivatives obtainable by this desired method should in this case be obtained preferably in high yield and high purity. In particular, the desired method should enable the desired target compounds to be obtained without the need for complex purification methods such as column chromatography. In particular, the desired method should enable the desired target compounds to be obtained without producing huge amounts of waste during the isolation of the target compounds, in particular not via the neutralization of $H_2SO_4$ by addition of NaOH.

SUMMARY

It has now been found, that 4-aminoindane derivatives can be prepared in high selectivity and under very mild conditions upon rearrangement of a compound of the formula (II) in anhydrous hydrogen fluoride (HF; CAS Registry Number: 7664-39-3). This is very surprising since no such reaction has been described to date and those skilled in the art would have expected that exposure to anhydrous HF would not lead to the desired 4-aminoindane since anhydrous HF is a weak acid compared to e.g. $H_2SO_4$. An additional advantage is that after the process is completed the excess of HF can be easily removed from the product using simple distillation at normal pressure and can finally even be recovered and recycled. Consequently, the production of huge amounts of waste is prevented by the present new preparation process.

Thus, the present invention relates to a novel process for preparing substituted 4-aminoindane derivatives of the general formula (I):

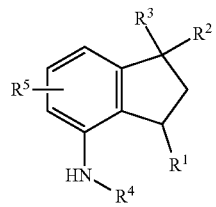
(I)

in which
$R^1$ is hydrogen, $(C_1-C_8)$-alkyl or $(C_3-C_8)$-cycloalkyl,
$R^2$, $R^3$ each are mutually independently hydrogen, $(C_1-C_8)$-alkyl or $(C_3-C_8)$-cycloalkyl,
$R^4$ is CO—$(C_1-C_4$-alkyl),
$R^5$ is hydrogen, halogen or $(C_1-C_4)$-alkyl,
characterized in that a compound of the Formula (II)

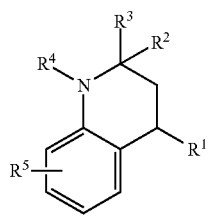
(II)

is reacted with anhydrous HF, wherein the definitions of the residues $R^1$, $R^2$, $R^3$, $R^4$ and $R^5$ listed in the formula (II) are the same as in the formula (I).

The present invention also relates to a novel process for preparing substituted 4-aminoindane derivatives of the general formula (I) as defined above in which
$R^1$ is methyl,
$R^2$, $R^3$ each are mutually independently hydrogen, $(C_1-C_8)$-alkyl or $(C_3-C_8)$-cycloalkyl,
$R^4$ is CO—$(C_1-C_4)$-alkyl,
$R^5$ is hydrogen, halogen or $(C_1-C_4)$-alkyl.
characterized in that a compound of the formula (II) as defined above is reacted with anhydrous HF, wherein the definitions of the residues $R^1$, $R^2$, $R^3$, $R^4$, and $R^5$ listed in the formula (II) are the same as in the formula (I).

Furthermore, the present invention also relates to a novel process for preparing substituted 4-aminoindane derivatives of the general formula (I) as defined above in which
$R^1$ is $(C_2-C_8)$-alkyl,
$R^2$, $R^3$ each are mutually independently hydrogen, $(C_1-C_8)$-alkyl or $(C_3-C_8)$-cycloalkyl,
$R^4$ is CO—$(C_1-C_4)$-alkyl,
$R^5$ is hydrogen, halogen or $(C_1-C_4)$-alkyl,
characterized in that a compound of the formula (II) as defined above is reacted with anhydrous HF, wherein the definitions of the residues $R^1$, $R^2$, $R^3$, $R^4$, and $R^5$ listed in the formula (II) are the same as in the formula (I).

DETAILED DESCRIPTION OF A PREFERRED EMBODIMENT

Preferred, particularly preferred and especially preferred definitions of the residues $R^1$, $R^2$, $R^3$, $R^4$ and $R^5$ listed in the formulae (I) and (II) mentioned above are elucidated below.

Preferred definitions of the residues $R^1$, $R^2$, $R^3$, $R^4$ and $R^5$ listed in the formulae (I) and (II) are:
$R^1$ is hydrogen or $(C_1-C_4)$-alkyl
$R^2$ and $R^3$ each are mutually independently hydrogen or $(C_1-C_4)$-alkyl,
$R^4$ is CO—$(C_1-C_4$-alkyl),
$R^5$ is hydrogen or $(C_1-C_4)$-alkyl.

Also preferred definitions of the residues $R^1$, $R^2$, $R^3$, $R^4$ and $R^5$ listed in the formulae (I) and (II) are:
$R^1$ is methyl,
$R^2$ and $R^3$ each are mutually independently hydrogen or $(C_1-C_4)$-alkyl,
$R^4$ is CO—$(C_1-C_4$-alkyl),
$R^5$ is hydrogen or $(C_1-C_4)$-alkyl.

Also preferred definitions of the residues $R^1$, $R^2$, $R^3$, $R^4$ and $R^5$ listed in the formulae (I) and (II) are:
$R^1$ is $(C_2-C_4)$-alkyl,
$R^2$ and $R^3$ each are mutually independently hydrogen or $(C_1-C_4)$-alkyl,
$R^4$ is CO—$(C_1-C_4$-alkyl),
$R^5$ is hydrogen or $(C_1-C_4)$-alkyl.

Particularly preferred definitions of the residues $R^1$, $R^2$, $R^3$, $R^4$ and $R^5$ listed in the formulae (I) and (II) are:
$R^1$ is hydrogen, methyl, ethyl, n-propyl, isopropyl or n-butyl,
$R^2$ and $R^3$ each are mutually independently methyl, ethyl, n-propyl, isopropyl or n-butyl,
$R^4$ is CO—$CH_3$ (i.e. acetyl),
$R^5$ is hydrogen or methyl.

Also particularly preferred definitions of the residues $R^1$, $R^2$, $R^3$, $R^4$ and $R^5$ listed in the formulae (I) and (II) are:
$R^1$ is methyl,
$R^2$ and $R^3$ each are mutually independently methyl, ethyl, n-propyl, isopropyl or n-butyl,
$R^4$ is CO—$CH_3$,
$R^5$ is hydrogen or methyl.

Also particularly preferred definitions of the residues $R^1$, $R^2$, $R^3$, $R^4$ and $R^5$ listed in the formulae (I) and (II) are:
$R^1$ is ethyl, n-propyl, isopropyl or n-butyl,
$R^2$ and $R^3$ each are mutually independently methyl, ethyl, n-propyl, isopropyl or n-butyl,
$R^4$ is CO—$CH_3$,
$R^5$ is hydrogen or methyl.

Especially preferred definitions of the residues $R^1$, $R^2$, $R^3$, $R^4$ and $R^5$ listed in the formulae (I) and (II) are:
$R^1$, $R^2$ and $R^3$ each are methyl,
$R^4$ is CO—$CH_3$,
$R^5$ is hydrogen.

Also especially preferred definitions of the residues $R^1$, $R^2$, $R^3$, $R^4$ and $R^5$ listed in the formulae (I) and (II) are:
$R^1$ is n-propyl,
$R^2$ and $R^3$ each are methyl,
$R^4$ is CO—$CH_3$
$R^5$ is hydrogen.

GENERAL DEFINITIONS

In the definitions of the symbols given in the above formulae, collective terms which are generally representative of the following substituents were used:

Halogen: fluorine, chlorine, bromine and iodine and preferably fluorine, chlorine, bromine and more preferably fluorine, chlorine.

Alkyl: saturated, straight-chain or branched hydrocarbyl radicals having 1 to 8, preferably 1 to 6 and more preferably 1 to 4 carbon atoms, for example (but not limited to) $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl. This definition also applies to alkyl as part of a composite substituent, for example cycloalkylalkyl, hydroxyalkyl etc., unless defined elsewhere. When the alkyl is at the end of a composite substituent as in alkylcycloalkyl for example, the part of the composite substituent at the start, for example the cycloalkyl, may be mono- or polysubstituted identically or differently and independently by alkyl. The same also applies to composite substituents in which other radicals, for example alkenyl, alkynyl, hydroxyl, halogen, formyl etc., are at the end.

Cycloalkyl: monocyclic, saturated hydrocarbyl groups having 3 to 8, preferably 3 to 6 carbon ring members, for example (but not limited to) cyclopropyl, cyclopentyl and cyclohexyl. This definition also applies to cycloalkyl as part of a composite substituent, for example cycloalkylalkyl etc., unless defined elsewhere.

DETAILED DESCRIPTION OF THE PROCESS

1-Acyl-trialkyl-3,4-dihydro-1H-quinolines of the formula (II) are known and can be prepared according to WO 2014/103811 (Reference Example 1-1 of WO 2014/103811).

The present inventive process is generally carried out at a temperature in the range of from −10° C. to 80° C., preferably in the range of from 0° C. to 50° C., more preferably in the range of from 0° C. to 40° C., most preferably in the range of from 0° C. to 30° C. and especially preferably at a temperature in the range of from 10° C. to 20° C.

The process is generally conducted at normal pressure or at elevated pressure in an autoclave.

The amount of anhydrous HF may be varied over a wide range but is preferably in the range of 1 to 100 molar equivalents, particularly preferably 5 to 30 molar equivalents and especially preferably 5 to 20 molar equivalents, in each case based on the total amount of compounds of the formula (II).

HF can be used in anhydrous form, as a solution in organic solvents (ethers, such as tetrahydrofuran (THF)) or as aqueous solution. Preferably, the process according to the invention is carried out in anhydrous HF.

The processes is preferably carried out without additional organic solvent, using anhydrous HF as a reagent and as solvent. But it is possible to replace a part of anhydrous HF by an organic solvent, in particular by ethers such as THF, dioxane, diethyl ether, diglyme, methyl tert-butyl ether (MTBE), tert-amyl methyl ether (TAME), dimethyl ether, 2-methyl-THF; nitriles such as acetonitrile (ACN) or butyronitrile; ketones such as acetone, methyl isobutyl ketone (MIBK); aromatic hydrocarbons such as toluene, anisole, xylenes, mesitylene; esters such as ethyl acetate, isopropyl acetate, butyl acetate, pentyl acetate; alcohols such as methanol, ethanol, propanol, butanol, ethylene glycol; carbonates such as ethylene carbonate, propylene carbonate; amides such as N,N-dimethylacetamide (DMAc), N,N-dimethylformamide (DMF), N-methylpyrrolidone; halohydrocarbons and halogenated aromatic hydrocarbons, particularly chlorohydrocarbons such as tetrachloroethylene, tetrachloroethane, dichloropropane, methylene chloride (dichloromethane, DCM), dichlorobutane, chloroform, carbon tetrachloride, trichloroethane, trichloroethylene, pentachloroethane, difluorobenzene, 1,2-dichloroethane, chlorobenzene, bromobenzene, dichlorobenzene, especially 1,2-dichlorobenzene, chlorotoluene, trichlorobenzene; fluorinated aliphatic and aromatic compounds such as trichlorotrifluoroethane, benzotrifluoride or 4-chlorobenzotrifluoride.

Preferably, HF is used in anhydrous form, optionally as solution in organic solvents, more preferably HF is used in anhydrous form with a boiling point of 20° C. (i.e. without any organic solvents and free of water).

The reaction time in anhydrous HF is not critical and it can generally be varied from 1 to 24 hours (h), preferably from 10 to 22 h.

According to the invention the starting material, i.e. a compound according to formula (II), is mixed with anhydrous HF and stirred for a certain time under a certain temperature as defined above. For the isolation of the product the excess of anhydrous HF preferably is removed using distillation and the (precipitated) product of formula (I) is obtained (filtered off).

Depending on the work up and isolation method of the reaction mixture obtained after reaction of the compound of the formula (II) with anhydrous HF, it is possible to get either a compound of the formula (I), wherein $R_4$ is CO—($C_1$-$C_4$-alkyl), or a compound of the formula (III), wherein $R_4$ is hydrogen, i.e. a free amine as illustrated in the process scheme and also in the preparation examples 1 and 2 below.

The compound of the formula (I) wherein $R_4$ is CO—($C_1$-$C_4$-alkyl) is isolated from the reaction mixture as a solid upon removal of HF via distillation. The solid is washed with cold water (5-10° C.) to remove the traces of HF and dried. In order to prepare a compound of the formula (III) wherein $R_4$ is H, water is added to the precipitate after the removal of HF and this mixture is heated to a temperature in the range of from 50° C. to 100° C., preferably in the range of from 60° C. to 100° C., especially preferably at a temperature in the range of from 80° C. to 100° C. for 6 to 10 h. After transformation, the pH of the medium is adjusted to 8 upon addition of aqueous solution of NaOH, the product is filtered off or extracted with organic solvent and dried. The amount of water may be varied over a wide range but is preferably in the range of from 1 to 100 molar equivalents, particularly preferably in the range of from 5 to 30 molar equivalents and especially preferably in the range of from 5 to 20 molar equivalents, in each case based on the total amount of compounds of the formula (I). The work up and isolation is generally conducted at normal pressure.

Process Scheme

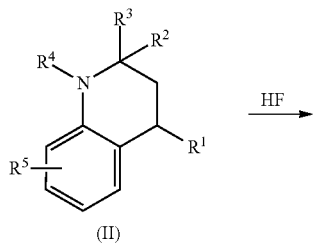

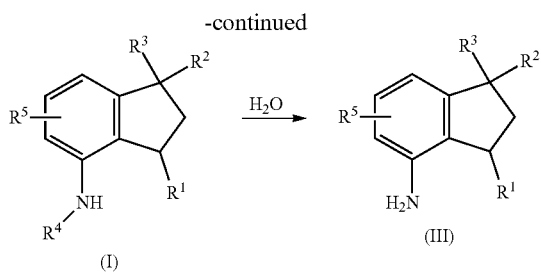

wherein in formulae (I), (II) and (III) the substituents $R^1$, $R^2$, $R^3$, $R^4$ and $R^5$ each have the general, preferred, particularly preferred or especially preferred meanings which have already been mentioned for these substituents in connection with the description of the compounds of the formulae (I), (II) and (III).

In the following, preferred embodiment of the present invention are described.

A first preferred embodiment is the process for preparing substituted 4-aminoindane derivatives of the general formula (I) as defined above, in which
$R^1$ is hydrogen, $(C_1-C_8)$-alkyl or $(C_3-C_8)$-cycloalkyl,
$R^2$, $R^3$ each are mutually independently hydrogen, $(C_1-C_8)$-alkyl or $(C_3-C_8)$-cycloalkyl,
$R^4$ is CO—$(C_1-C_4)$-alkyl,
$R^5$ is hydrogen, halogen or $(C_1-C_4)$-alkyl,
characterized in that a compound of the Formula (II) as defined above, is reacted with anhydrous HF at a temperature in the range of from 0° C. to 30° C., wherein the definitions of the residues $R^1$, $R^2$, $R^3$, $R^4$ and $R^5$ listed in the formula (II) are the same as in the formula (I).

A second preferred embodiment is the process for preparing substituted 4-aminoindane derivatives of the general formula (I) as defined above, in which
$R^1$ is methyl,
$R^2$, $R^3$ each are mutually independently hydrogen, $(C_1-C_8)$-alkyl or $(C_3-C_8)$-cycloalkyl,
$R^4$ is CO—$(C_1-C_4)$-alkyl,
$R^5$ is hydrogen, halogen or $(C_1-C_4)$-alkyl,
characterized in that a compound of the Formula (II) as defined above is reacted with anhydrous HF at a temperature in the range of from 0° C. to 30° C., wherein the definitions of the residues $R^1$, $R^2$, $R^3$, $R^4$ and $R^5$ listed in the formula (II) are the same as in the formula (I).

A third preferred embodiment is the process for preparing substituted 4-aminoindane derivatives of the general formula (I) as defined above, in which
$R^1$ is $(C_2-C_8)$-alkyl,
$R^2$, $R^3$ each are mutually independently hydrogen, $(C_1-C_8)$-alkyl or $(C_3-C_8)$-cycloalkyl,
$R^4$ is CO—$(C_1-C_4)$-alkyl,
$R^5$ is hydrogen, halogen or $(C_1-C_4)$-alkyl,
characterized in that a compound of the Formula (II) as defined above is reacted with anhydrous HF at a temperature in the range of from 0° C. to 30° C., wherein the definitions of the residues $R^1$, $R^2$, $R^3$, $R^4$ and $R^5$ listed in the formula (II) are the same as in the formula (I).

A fourth preferred embodiment is the process for preparing substituted 4-aminoindane derivatives of the general formula (I) as defined above, in which
$R^1$ is hydrogen or $(C_1-C_4)$-alkyl
$R^2$ and $R^3$ each are mutually independently hydrogen or $(C_1-C_4)$-alkyl,
$R^4$ is CO—$(C_1-C_4$-alkyl),
$R^5$ is hydrogen or $(C_1-C_4)$-alkyl,
characterized in that a compound of the Formula (II) as defined above is reacted with anhydrous HF at a temperature in the range of from 0° C. to 30° C., wherein the definitions of the residues $R^1$, $R^2$, $R^3$, $R^4$ and $R^5$ listed in the formula (II) are the same as in the formula (I).

A fifth preferred embodiment is the process for preparing substituted 4-aminoindane derivatives of the general formula (I) as defined above, in which
$R^1$ is methyl,
$R^2$ and $R^3$ each are mutually independently hydrogen or $(C_1-C_4)$-alkyl,
$R^4$ is CO—$(C_1-C_4$-alkyl),
$R^5$ is hydrogen or $(C_1-C_4)$-alkyl,
characterized in that a compound of the Formula (II) as defined above is reacted with anhydrous HF at a temperature in the range of from 0° C. to 30° C., wherein the definitions of the residues $R^1$, $R^2$, $R^3$, $R^4$ and $R^5$ listed in the formula (II) are the same as in the formula (I).

A sixth preferred embodiment is the process for preparing substituted 4-aminoindane derivatives of the general formula (I) as defined above, in which
$R^1$ $(C_2-C_4)$-alkyl,
$R^2$ and $R^3$ each are mutually independently hydrogen or $(C_1-C_4)$-alkyl,
$R^4$ is CO—$(C_1-C_4$-alkyl),
$R^5$ is hydrogen or $(C_1-C_4)$-alkyl,
characterized in that a compound of the Formula (II) as defined above is reacted with anhydrous HF at a temperature in the range of from 0° C. to 30° C., wherein the definitions of the residues $R^1$, $R^2$, $R^3$, $R^4$ and $R^5$ listed in the formula (II) are the same as in the formula (I).

A seventh preferred embodiment is the process for preparing substituted 4-aminoindane derivatives of the general formula (I) as defined above, in which
$R^1$ hydrogen, methyl, ethyl, n-propyl, isopropyl or n-butyl,
$R^2$ and $R^3$ each are mutually independently methyl, ethyl, n-propyl, isopropyl or n-butyl,
$R^4$ is CO—$CH_3$ (i.e. acetyl),
$R^5$ is hydrogen or methyl,
characterized in that a compound of the Formula (II) as defined above is reacted with anhydrous HF at a temperature in the range of from 0° C. to 30° C., wherein the definitions of the residues $R^1$, $R^2$, $R^3$, $R^4$ and $R^5$ listed in the formula (II) are the same as in the formula (I).

An eighth preferred embodiment is the process for preparing substituted 4-aminoindane derivatives of the general formula (I) as defined above, in which
$R^1$ is methyl,
$R^2$ and $R^3$ each are mutually independently methyl, ethyl, n-propyl, isopropyl or n-butyl,
$R^4$ is CO—$CH_3$,
$R^5$ is hydrogen or methyl,
characterized in that a compound of the Formula (II) as defined above is reacted with anhydrous HF at a temperature in the range of from 0° C. to 30° C., wherein the definitions of the residues $R^1$, $R^2$, $R^3$, $R^4$ and $R^5$ listed in the formula (II) are the same as in the formula (I).

A ninth preferred embodiment is the process for preparing substituted 4-aminoindane derivatives of the general formula (I) as defined above, in which
$R^1$ is ethyl, n-propyl, isopropyl or n-butyl,
$R^2$ and $R^3$ each are mutually independently methyl, ethyl, n-propyl, isopropyl or n-butyl,
$R^4$ is CO—$CH_3$,
$R^5$ is hydrogen or methyl,
characterized in that a compound of the Formula (II) as defined above is reacted with anhydrous HF at a temperature in the range of from 0° C. to 30° C., wherein the definitions of the residues $R^1$, $R^2$, $R^3$, $R^4$ and $R^5$ listed in the formula (II) are the same as in the formula (I).

A tenth preferred embodiment is the process for preparing substituted 4-aminoindane derivatives of the general formula (I) as defined above, in which
$R^1$, $R^2$ and $R^3$ each are methyl,
$R^4$ is CO—CH$_3$,
$R^5$ is hydrogen,
characterized in that a compound of the Formula (II) as defined above is reacted with anhydrous HF at a temperature in the range of from 0° C. to 30° C., wherein the definitions of the residues $R^1$, $R^2$, $R^3$, $R^4$ and $R^5$ listed in the formula (II) are the same as in the formula (I).

An eleventh preferred embodiment is the process for preparing substituted 4-aminoindane derivatives of the general formula (I) as defined above, in which
$R^1$ is n-propyl,
$R^2$ and $R^3$ each are methyl,
$R^4$ is CO—CH$_3$
$R^5$ is hydrogen,
characterized in that a compound of the Formula (II) as defined above is reacted with anhydrous HF at a temperature in the range of from 0° C. to 30° C., wherein the definitions of the residues $R^1$, $R^2$, $R^3$, $R^4$ and $R^5$ listed in the formula (II) are the same as in the formula (I).

PREPARATION EXAMPLES

Example 1: Synthesis of N-(1,1,3-trimethylindan-4-yl)acetamide (a Compound of Formula (I))

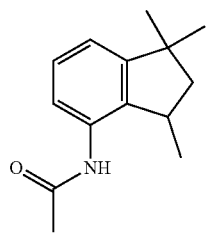 [SMILES: CC(=O)Nc1cccc2c1C(C)CC2(C)C]

80 g of anhydrous hydrogen fluoride (HF) was initially charged in a 250 mL teflon reactor and cooled to 0° C. 21.7 g (0.1 mol) of 1-(2,2,4-trimethyl-3,4-dihydroquinolin-1-yl)ethanone were added and the reaction mixture was allowed to warm slowly to 15° C. within 1 h. The reaction mixture was stirred at this temperature for 20 h and 70-75 g of HF was then distilled off and recovered. The solid which precipitated was filtered off and washed three times with 20 ml of cold water and dried to give 21 g of N-(1,1,3-trimethyl-indan-4-yl)acetamide (97% yield) as pale yellow solid with a melting point (m.p.) of 115-116° C.

$^1$H NMR (DMSO) δ: 9.31; (s, 1H), 7.22; (d, 1H), 7.12; (t, 1H), 6.95; (d, 1H), 3.40; (m, 1H), 2.13; (dd, 1H) 2.03; (s, 3H), 1.51; (dd, 1H), 1.28; (s, 3H), 1.18; (d, 3H), 1.15; (s, 3H) ppm.

Likewise, the compound N-(1,1-dimethyl-3-propylindan-4-yl)acetamide, wherein $R^1$ is propyl, could be obtained with this process.

Compared to the processes known from EP 0654464 and Cliffe et al. (*J. Chem. Soc.* (C), 1966, 514-517: "*The Acid-catalyzed Rearrangement of Tetrahydroquinoline Derivatives*") the process according to the invention leads to a decreased amount of waste:

According to EP 0654464, 55 g of the starting material were used in reaction with 50 ml (i.e. 90 g) of concentrated H$_2$SO$_4$. To isolate the product (4-amino-1,1,3-trimethylindane), 50 ml (i.e. 50 g) of water and 150 ml of ammonia (35% solution in water; i.e. 150 g) were added (to form ammonia sulfate) and the product was isolated upon extraction. In conclusion, for 22 g of the obtained product 290 g liquid waste (water solution of ammonium sulfate) were produced which equals 1 g of desired product per 13 g of liquid waste.

Cliffe et al. describe the rearrangement of quinolines into aminoindane derivatives upon heating with H$_2$SO$_4$. For the preparation of 1 g of the product 10 g of H$_2$SO$_4$ (concentrated) are needed producing after work up at least 50-100 g of diluted H$_2$SO$_4$. Although not explicitly disclosed in the document, this diluted H$_2$SO$_4$ should be completely neutralized in order to isolate the desired aminoindane derivatives, which easily form a water soluble salt with H$_2$SO$_4$. In conclusion, also the process according to Cliffe et al. presumably produces higher amounts of liquid waste per unit of product.

Contrary to that, the process according to the present invention consumes maximum 1 equivalent of anhydrous HF based on the total amount of employed reactant and the excess of HF used for the rearrangement can be completely recovered.

Example 2 (reference example): Synthesis of 1,1,3-trimethyl-indan-4-amine (a Compound of Formula (III))

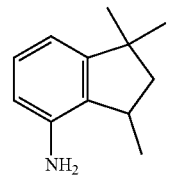

80 g of anhydrous hydrogen fluoride was initially charged in a 250 mL teflon reactor and cooled to 0° C. 21.7 g (0.1 mol) of 1-(2,2,4-trimethyl-3,4-dihydroquinolin-1-yl)ethanone were added and the reaction mixture allowed to warm slowly to 19° C. The reaction mixture was stirred at this temperature for 20 h and 70-75 g of HF was then distilled off 60 g of water were added and the mixture was heated for 6 h at 100° C. Then the pH of the solution was adjusted to 8 with 4-5 ml of 40% NaOH solution in water and the product extracted with ethylacetate. Organic solvent was evaporated to give 15.7 (90%) of 1,1,3-trimethyl-indan-4-amine as pale yellow oil.

Mass spectra: m/z 175.

Likewise, the compound 1,1-dimethyl-3-propylindan-4-amine, wherein $R^1$ is propyl, could be obtained with this process.

Example 3 (Reference Example): Synthesis of 1,1,3-trimethyl-indan-4-amine (a Compound of Formula (III)) with HF Recovery

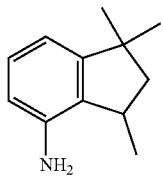

80 g of anhydrous hydrogen fluoride was initially charged in a 250 mL teflon reactor and cooled to 0° C. 21.7 g (0.1 mol) of 1-(2,2,4-trimethyl-3,4-dihydroquinolin-1-yl)ethanone were added and the reaction mixture allowed to warm slowly to 19° C. The reaction mixture was stirred at this temperature for 20 h and 70 ml Toluene were added. HF was then distilled off under normal pressure at 30-40° C. collecting (75-78 g) of HF. 60 g of water were added and two phase mixture was heated for 6 h at 100° C. Then the pH of the solution was adjusted to 8 with 2-3 ml of 40% NaOH solution in water, organic phase separated and toluene removed in vacuum to give 16 g of 1,1,3-trimethyl-indan-4-amine as pale yellow oil.

Mass spectra: m/z 175.

The invention claimed is:

1. A process for preparing substituted 4-aminoindane derivative of general formula (I)

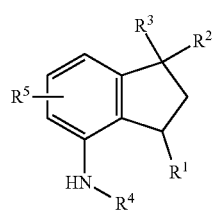

in which
$R^1$ is hydrogen, $(C_1-C_8)$-alkyl or $(C_3-C_8)$-cycloalkyl,
$R^2$, $R^3$ each are mutually independently hydrogen, $(C_1-C_8)$-alkyl or $(C_3-C_8)$-cycloalkyl,
$R^4$ is CO—$(C_1-C_4)$-alkyl,
$R^5$ is hydrogen, halogen or $(C_1-C_4)$-alkyl,
comprising reacting a compound of Formula (II)

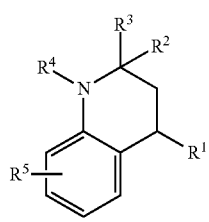

with anhydrous hydrogen fluoride.

2. The process according to claim 1, wherein
$R^1$ is hydrogen or $(C_1-C_4)$-alkyl
$R^2$ and $R^3$ each are mutually independently hydrogen or $(C_1-C_4)$-alkyl,
$R^4$ is CO—$(C_1-C_4)$-alkyl,
$R^5$ is hydrogen or $(C_1-C_4)$-alkyl.

3. The process according to claim 1, wherein
$R^1$ is hydrogen, methyl, ethyl, n-propyl, isopropyl or n-butyl,
$R^2$ and $R^3$ each are mutually independently methyl, ethyl, n-propyl, isopropyl or n-butyl,
$R^4$ is CO—$CH_3$,
$R^5$ is hydrogen or methyl.

4. The process according to claim 1, wherein
$R^1$, $R^2$ and $R^3$ each are methyl,
$R^4$ is CO—$CH_3$,
$R^5$ is hydrogen.

5. The process according to claim 1, wherein the process is carried out at a temperature in a range of from 0° C. and 50° C.

6. The process according to claim 1, wherein the process is carried out at a temperature in a range of from 0° C. and 40° C.

7. The process according to claim 1, wherein the process is carried out at a temperature in a range of from 0° C. and 30° C.

8. The process according to claim 1, wherein the process is carried out at a temperature in a range of from 10° C. and 20° C.

9. The process according to claim 1, wherein an amount of used hydrogen fluoride is in the range of 1 to 100 molar equivalents based on the total amount of compound of formula (II).

10. The process according to claim 1, wherein reaction time of hydrogen fluoride with compounds of formula (II) is between 1 and 24 hours.

11. A process for preparation of a compound of formula (III)

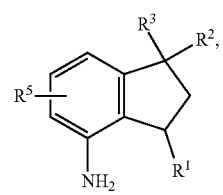

wherein
$R^1$ is hydrogen, $(C_1-C_8)$-alkyl or $(C_3-C_8)$-cycloalkyl,
$R^2$, $R^3$ each are mutually independently hydrogen, $(C_1-C_8)$-alkyl or $(C_3-C_8)$-cycloalkyl,
$R^4$ is CO—$(C_1-C_4)$-alkyl,
$R^5$ is hydrogen, halogen or $(C_1-C_4)$-alkyl,
comprising the process according to claim 1 and further comprising hydrolyzing the compound of formula (I) in water to obtain the compound of formula (III).

12. The process according to claim 11, wherein the process is carried out at a temperature in a range of from 50° C. to 100° C.

13. The process according to claim 1, wherein an amount of used hydrogen fluoride is in a range of 5 to 30 molar equivalents based on the total amount of compound of formula (II).

14. The process according to claim 1, wherein an amount of used hydrogen fluoride is in a range of 5 to 20 molar equivalents based on the total amount of compound of formula (II).

15. The process according to claim 1, wherein a reaction time of hydrogen fluoride with compounds of formula (II) is between 10 and 22 hours.

\* \* \* \* \*